United States Patent [19]

Gnehm et al.

[11] Patent Number: 4,652,659

[45] Date of Patent: * Mar. 24, 1987

[54] METHOD FOR THE PRODUCTION OF ACEMETACIN

[75] Inventors: René Gnehm, Küngoldingen; Rolf Weber, Zofingen, both of Switzerland

[73] Assignee: Siegfried Aktiengesellschaft, Zofingen, Switzerland

[*] Notice: The portion of the term of this patent subsequent to Mar. 5, 2002 has been disclaimed.

[21] Appl. No.: 661,537

[22] Filed: Oct. 16, 1984

Related U.S. Application Data

[63] Continuation-in-part of Ser. No. 450,507, Dec. 16, 1982, Pat. No. 4,503,237.

[30] Foreign Application Priority Data

Dec. 28, 1981 [CH] Switzerland ............... 8306/81

[51] Int. Cl.$^4$ .................................... C07D 209/28
[52] U.S. Cl. ...................................... 548/501; 548/500
[58] Field of Search ......................................... 548/501

[56] References Cited

U.S. PATENT DOCUMENTS

4,503,237  3/1985  Gnehm et al. ............... 548/501

FOREIGN PATENT DOCUMENTS

837084   3/1970   Canada ......................... 548/449
0126942  12/1984  European Pat. Off. ........ 548/501

Primary Examiner—Glennon H. Hollrah
Assistant Examiner—W. B. Springer
Attorney, Agent, or Firm—Jordan and Hamburg

[57] ABSTRACT

1-(4-Chlorobenzoyl)-5-methoxy-2-methyl-1H-indole-3-acetic acid carboxymethyl ester as known per se is obtainable by a novel and more simple method comprising mild acid hydrolysis of 1-(4-chlorobenzoyl)-5-methoxy-2-methyl-1H-indole-3-acetoxyacetic tetrahydropyran-2-yl ester. The final product is a valuable drug having antiinflammatory activity.

5 Claims, No Drawings

METHOD FOR THE PRODUCTION OF ACEMETACIN

REFERENCE TO RELATED APPLICATION

This is a continuation-in-part of application Ser. No. 450,507 filed Dec. 16, 1982, now U.S. Pat. No. 4,503,237.

BACKGROUND OF THE INVENTION

The present invention relates to a process for preparing an indole derivative, namely 1-(4-chlorobenzoyl)-5-methoxy-2-methyl-1H-indole-3-acetic acid carboxymethyl ester. The process substantially follows a sequence of reaction steps known per se and including the esterification of 1-(4-chlorobenzoyl)-5-methoxy-2-methyl-1H-indole-acetic acid with a chloroacetic acid derivative carrying a protective group on its carboxyl group followed by splitting off the protective group.

The 1-(4-chlorobenzoyl)-5-methoxy-2-methyl-1H-indole-3acetic acid carboxymethyl ester, for which the World Health Organization recommends the International Nonproprietary Name acemetacin, is disclosed in the German Laying-Open-Specification DE No. 22 34 651 A1 as an antiinflammatory active drug representing a valuable modification of the 1-(4-chlorobenzoyl)-5-methoxy-2-methyl-1H-indole-3-acetic acid, which latter is used in the therapeutic practice, and for which the International Nonproprietary Name indometacin is well accepted.

From the above names of both compounds according to systematic nomenclature acemetacin obviously can be understood to be a derivative of indometacin resulting from an esterification of the carboxyl group of indometacin with the α-hydroxyl group of glycolic acid.

As is obvious for the expert, such a direct esterification cannot be carried out in practice; instead, glycolic acid must be replaced by a carboxylic acid carrying on its α-carbon atom especially a chlorine atom instead of the hydroxyl group and a suitable protective group on its carboxyl radical. The proper choice of the protective group is of paramount importance, since under the reaction conditions else used for splitting off a standard protective group at least the other ester bond of the desired final product is split, too, while additionally other groups or radicals of the quite delicate molecule tend to be modified.

For solving this problem a benzyl radical is used as the protective group in the method disclosed in DE No. 22 34 651 A1. The benzyl radical, when used as the protective group, can be split off hydrogenolytically while simultaneously substantially not effecting the remaining moieties of the molecule.

The aforementioned reference also discloses additional alternative ways for preparing acemetacin which methods do not use indometacin as an intermediate. All these methods, however, have the common feature that the last intermediate in the respective sequence of reaction steps carries a benzyl group protecting the carboxyl group, which benzyl group then must be split off hydrogenolytically in a final reaction step.

The method of hydrogenolytic cleavage, however, implies a considerable technical effort if compared to an ester cleavage via hydrolysis. Also the results obtainable with the hydrogenolytic cleavage are not really efficient, since under the necessary reaction conditions the chlorine atom of the chlorobenzoyl substituent also is split off, at least partially. In practice, the different methods using hydrogenolytic debenzylation obviously were disadvantageous to such an extent that a few years later a method for producing acemetacin was developed (cf. DE No. 29 43 125 A1) based on a planned and careful synthesis of the indole structure itself, in which method α-(chlorobenzoyl)-4methoxyphenylhydrazine hydrochloride is reacted with benzyl levulinate to yield the corresponding hydrazone, which in turn is subject to a cyclocondensation splitting off ammonia, and yielding the desired final product having an unprotected carboxyl group.

SUMMARY OF THE INVENTION

In accordance with the present invention there is now provided a process for preparing acemetacin via indometacin, in which the necessary protective group is a protective group which can be split off by means of a simple hydrolysis allowing for such mild reaction conditions that none of the remaining bonds in the molecule is attacked or is influenced at all so that substantially no side reaction products are formed during this hydrolytic cleavage reaction. According to the present invention the protective group is the 2-tetrahydropyranyl radical.

The method of the invention thus is characterized in that 1-(4-chlorobenzoyl)-5-methoxy-2-methyl-1H-indole-3-acetoxyacetic acid tetrahydropyran-2-yl ester is subject to a conventional mild acid hydrolysis. For carrying out the hydrolysis reaction diluted aqueous inorganic and organic acids can be used, such as sulfuric, phosphoric, hydrochloric, hydrobromic, acetic, propionic, benzoic and the like acids as commonly applied in mild acid hydrolysis reactions. Preferred acids are hydrochloric and acetic acids.

The concentration of the acid in the reaction mixture is typically in the range of about 3 to about 50% by weight, preferably in the range of 5to 35% by weight. The reaction temperature is preferably held at above 10° C. and below a temperature of about 80° C. and especially is held in the range from about 20° C. to about 60° C. When carrying out the acid hydrolysis in the presence of hydrochloric acid, a temperature in the range of 25° C. to 40° C. is preferably maintained, while a temperature in the range of 40° C. to 60° C. is preferably maintained, when acetic acid is used. When using HCl, a concentration of about 10 to 15 wt.-% is preferred.

DETAILED DESCRIPTION OF THE INVENTION 1-(4-Chlorobenzoyl)-5-methoxy-2-methyl-1H-indole-3-acetoxyacetic tetrahydropyran-2-yl ester is used as the starting material for carrying out the process of the invention. This tetrahydropyran-2-yl ester is a novel compound. It can be easily prepared by well-known methods, which can be carried out by the expert without any difficulty. For instance, 1-(4-chlorobenzoyl)-5-methoxy-2-methyl-1H-indole-3-acetic acid can be esterified with 2-tetrahydropyranyl chloroacetate, i.e. with the chloroacetic acid tetrahydropyran-2-yl ester forming the 1-(4-chlorobenzoyl)-5-methoxy-2-methyl-1H-indole3-acetoxy acetic tetrahydropyran-2-yl ester with a yield almost equal to the theoretical one.

The chloroacetic acid tetrahydropyran-2-yl ester is a novel compound, too. As shown in the more detailed description below, this novel chloroacetic acid tetrahydropyran-2-yl ester easily is obtainable in an analogous manner to well-known reactions. Nevertheless, for the sake of completeness a method of producing the chloroacetic acid tetrahydropyran-2-yl ester is described in detail in the following examples as the first step in a sequence of reaction steps yielding acemetacin, i.e. 1-(4-chlorobenzoyl)-5-methoxy-2-methyl-1H-indole-3-acetic acid carboxymethyl ester as the desired final product.

The equations showing the preparation of the present compounds are given below:

Formular Flow Chart of Reaction Steps

1st Step

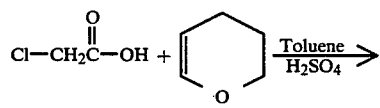

2nd Step

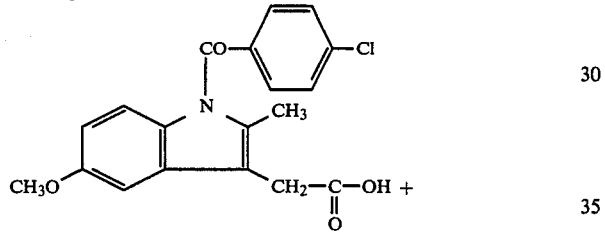

3rd Step

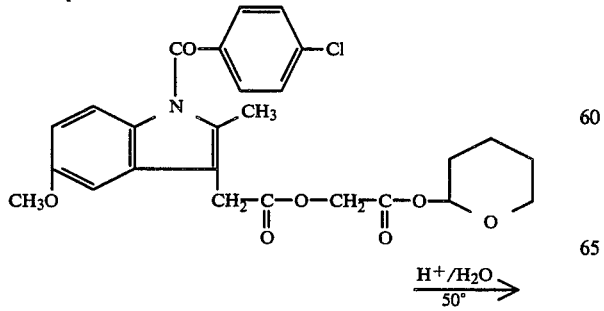

-continued
Formular Flow Chart of Reaction Steps

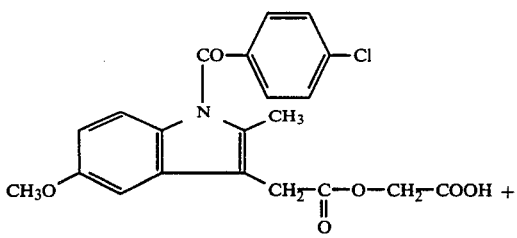

EXAMPLE 1

1st Reaction Step

Preparation of chloroacetic acid tetrahydropyran-2-yl ester

A mixture of 185 g (2.2 mol) 3,4-dihydro-2H-pyrene, 200 ml toluene and 0.2 ml concentrated sulfuric acid is added dropwise over a period of 15 min at a temperature of 15° C. with a solution of 142 g (1.5 mol) chloroacetic acid in 500 ml toluene. During the addition ice-cooling is provided. After finishing the addition of the chloroacetic acid solution the reaction mixture is stirred 2 h at room temperature. 15 g anhydrous potassium carbonate are added for stabilizing purposes. The reaction mixture thus stabilized then is evaporated in a rotating evaporator at 45° C. applying the vacuum of water-jet vacuum pump. Having thus stripped off the lower boiling volatile components a mixture of the tetrahydropyran-2-yl ester and potassium carbonate in an amount of 283 g is obtained as a residue. Based on the chloroacetic acid the yield is 100%.

Prior to using the thus obtained chloroacetic acid tetrahydropyran-2-yl ester as the starting material in the next reaction step the stabilizing agent, in this case potassium carbonate, can (but need not) be separated by filtration.

2nd Reaction Step

Preparation of 1-(4-chlorobenzoyl)-5-methoxy-2-methyl-1H-indole-3-acetoxyacetic acid) tetrahydropyran-2-yl ester (Acemetacin-tetrahydropyran-2-yl ester)

107.3 g (0.3 mol) Indometacin, i.e. 1-(4-chlorobenzoyl)-5-methoxy-2-methyl-1H-indole-3-acetic acid, are dissolved in 215 ml dimethylformamide and 15 min stirred at 55° C. with 30 g (0.22 mol) anhydrous potassium carbonate. While maintaining this temperature of 55° C., 54 g (0.3 mol) of chloroacetic acid tetrahydrophyran-2-yl ester obtained in step 1 are added dropwise during a period of 20 min. After 1 h there are added another 18 g (0.1 mol) of tetrahydropyran-2-yl ester, and then stirring is continued for 2.5 h at 55° C. The reaction mixture thus obtained is hydrolized in the 3rd reaction step without separating and recovering the acemetacin-tetrahydropyran-2-yl ester formed.

3rd Reaction Step

Preparation of acemetacin
(1-(4-chlorobenzoyl)-5-methoxy-2-methyl-1H-indole-3-acetic acid carboxymethyl ester)

To the reaction mixture obtained in the 2nd reaction step are added 100 ml acetic acid having a concentration of 98% and 30 ml water. The mixture then is stirred 2 h at a temperature of 50° C. The mixture then is cooled down to 30° C. and diluted with 220 ml water until the solution starts to become turbid. The reaction mixture then is stirred and kept over night at room temperature for the crystallization of crude acemetacin. For the purification of the thus obtained crude acemetacin 122 g of the dried crude material (94 % based on the weight of indometacin used) are re-crystallized in a manner known per se, for instance as disclosed in DE No. 29 43 127 A1, according to which the crude material is dissolved in acetone, from which solution the acemetacin then is precipitated by adding water. After drying the precipitate at 75° C. under a pressure of 8 mbar a purified anhydrous acemetacin is obtained having a melting point of 150°–152° C.

EXAMPLE 2

One-pot preparation of
acemetacin(1-(4-chlorobenzoyl)-5-methoxy2-methyl-1H-indole-3-acetic acid carboxymethyl ester)

An enamel coated steel reactor having a capacity of 500 l is charged with 230 kg acetone. Under a nitrogen atmosphere 40.60 kg indometacin and 14.9 kg potassium carbonate are added. The mixture then is heated under reflux to 50 to 55° C. At this temperature 31.10 kg chloroacetic acid tetrahydropyran-2-yl ester is added slowly over a period of 10 min. While stirring the reaction mixture then is refluxed at 55° C. for 2 h. After stripping 130 kg acetone over a period of about 1.5 h the reaction mixture again is refluxed for about 5 h for completing the reaction. Still under nitrogen atmosphere the reaction mixture then is cooled down to 25° C.

At ambient temperature (about 25 ° C.) a solution of 14.80 kg technical hydrochloric acid having a concentration of 32%.-wt. in 32.50 kg of water is added so that the $CO_2$ formation is well controlled. When pH 2 is established, the reaction mixture is heated to 35° C. and stirred at this temperature for 2 h. After adding 57 kg of water the temperature again is raised to 30° C. When the organic and the aqueous phases are well separated, the lower aqueous phase is discharged. The remaining organic acetone phase is added with another 71 kg water and cooled to 15° C. While stirring the reaction mixture at 15° C. some acemetacin seed crystals are added, whereupon the product is allowed to crystallize over a period of 4 h at 15° C. The solids are separated from the liquid phase and washed with a mixture of 10 kg of acetone and 10 kg of water. After drying 41 kg of slightly yellowish crude acemetacin are obtained.

The crude product obtained is re-crystallized from 170 kg of acetone. After washing the separated crystals with 10 kg of acetone in 12 kg of water there are obtained white crystals which are dried under vacuum at 70° C. This yields 31 kg of pure greenish-yellow acemetacin crystals having a melting point of 152.5° C.

We claim:

1. A process for producing 1-(4-chlorobenzoyl)-5-methoxy2-methyl-1H-indole-3-acetic acid carboxymethyl ester comprising mild acid hydrolysis of 1-(4-chlorobenzoyl)5-methoxy-2-methyl-1H-indole-3-acetoxyacetic acid tetrahydropyran-2-yl ester at a temperature in the range of above about 10° C. and below about 80° C.

2. The process of claim 1, wherein the temperature of the hydrolysis is in the range from about 20° C. to about 60° C.

3. The process of claim 1, wherein the hydrolysis is carried out in the presence of diluted aqueous hydrochloric acid.

4. The process of claim 1, wherein the hydrolysis is carried out in the presence of diluted aqueous acetic acid.

5. The process of claim 3, wherein the concentration of HCl in the reaction system is from about 10% to about 15% by weight and the temperature is in the range from about 20 ° C. to about 40° C.

* * * * *